United States Patent [19]

Kanamaru et al.

[11] Patent Number: 4,963,581

[45] Date of Patent: Oct. 16, 1990

[54] NAPHTHOPYRAN DERIVATIVES AND USE THEREOF

[75] Inventors: Tsuneo Kanamaru; Takenori Ishimaru; Masayuki Muroi, all of Osaka, Japan

[73] Assignee: Takeda Chemical Industries, Ltd., Osaka, Japan

[21] Appl. No.: 333,248

[22] Filed: Apr. 5, 1989

[30] Foreign Application Priority Data

Apr. 15, 1988 [JP] Japan .................................. 63-94170

[51] Int. Cl.$^5$ .................. C07D 311/92; A61K 31/365
[52] U.S. Cl. ..................................... 514/455; 549/280
[58] Field of Search ......................... 549/280; 514/455

[56] References Cited

U.S. PATENT DOCUMENTS 4,537,858  8/1985  O'Sullivan et al. ................. 549/280

OTHER PUBLICATIONS

Akita et al., CA 91: 205062x.
Zeeck et al., CA 91: 20250p.
Sedmera et al., CA 96: 84032e.
Singh et al., CA 103: 140195n.
Pushpa Singh et al., "Two New Inhibitors of Phospholipase A$_2$ Produced by Penicillium Chermesinum: Taxonomy, Fermentation, Isolation, Structure Determination and Biological Properties", The Journal of Antibiotics, vol. 38(6), pp. 706-712 (1985).
Axel Zeeck et al., "Isolierung des Antibioticums Semi--Vioxanthiaus Penicillium Citreo-Viride und Synthese des Xanthomegnins", Chem. Ber., vol. 112, pp. 957-978 (1979).

Primary Examiner—Jane T. Fan
Attorney, Agent, or Firm—Wegner & Bretschneider

[57] ABSTRACT

The present invention relates to an aromatase inhibiting composition which contains a compound of the formula:

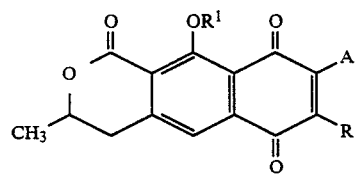

wherein R is hydroxy, lower alkoxy or amino which may be substituted by lower alkyl; $R^1$ is hydrogen or lower alkyl; and A is hydrogen, a group of the formula

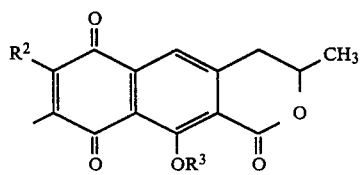

in which $R^2$ is hydroxy, lower alkoxy or amino which may be substituted by lower alkyl and $R^3$ is hydrogen or lower alkyl, or a group of the formula

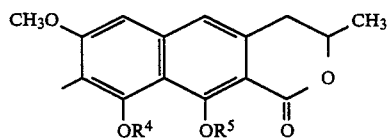

in which $R^4$ and $R^5$ are independently hydrogen or lower alkyl, or a salt thereof.

The present composition is useful in the prevention and treatment of estrogen-dependent diseases, such as breast cancer.

11 Claims, No Drawings

NAPHTHOPYRAN DERIVATIVES AND USE THEREOF

This invention relates to naphthopyran derivatives and use thereof.

It is known that the enzyme aromatase catalyzes the biosynthesis of estrogen from androgen. It is thought that efficient inhibition of the aromatase enzyme can be effective in the treatment and prevention of estrogen-dependent diseases, for example breast cancer, in mammals [cf. Cancer Research, 42, 3261s (1982)].

The estrogen-dependent diseases which can be treated or prevented with aromatase inhibitors includes, in addition to breast cancer, endometriosis, carcinoma of uterine body, ovarian cancer, polycystic ovary syndrome and prostatomegaly, among others. Aromatase inhibitors are also useful in conception control. Particularly in the treatment of breast cancer, aromatase inhibitors are said to be possibly useful as alternatives to ovariectomy, adrenalectomy and the like conventional therapies.

The aromatase inhibitors currently under clinical trial as therapeutic agents for breast cancer and so forth include, among others, aminoglutethimide, which is a nonsteroid, and 4-hydroxy-androstenedione and testolactone, which are steroids. Aminoglutethimide, however, is disadvantageous in that it inhibits various enzymes involved in the biosynthesis of steroid hormones, whereas steroidal drugs may expectedly produce adverse pharmacological effects characteristic of steroids.

As a result of their investigations made in search of an aromatase inhibitor differing in structure from the above-mentioned medicinals, the present inventors found that certain naphthopyran compounds inhibit said enzyme and lowers the blood estrogen level and, based on this finding, they have now completed the present invention.

The invention provides aromatase inhibitors which contain a compound of the general formula:

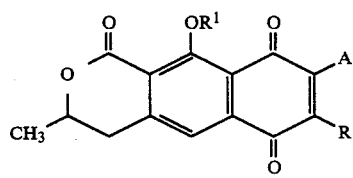
(I)

Wherein R is hydroxy, lower alkoxy or amino which may be substituted by lower alkyl; $R^1$ is hydrogen or lower alkyl; and A is hydrogen, a group of the formula

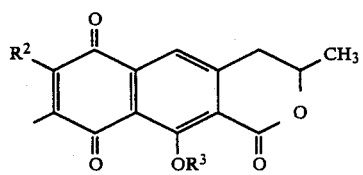

in which $R^2$ is hydroxy, lower alkoxy or amino which may be substituted by lower alkyl and $R^3$ is hydrogen or lower alkyl, or a group of the formula

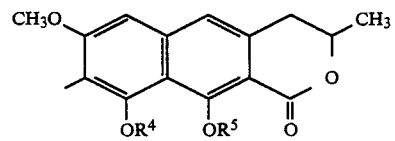

in which $R^4$ and $R^5$ are independently hydrogen or lower alkyl, or a salt thereof.

The invention also provides compounds of the general formula:

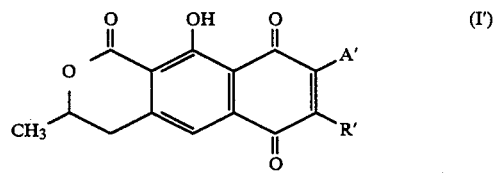
(I')

wherein R' is lower alkoxy containing at least 2 carbon atoms or amino which may be substituted by lower alkyl and A', is a group of the formula

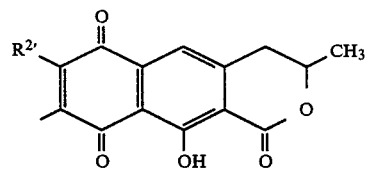

in which $R^{2'}$ is hydroxy, lower alkoxy or amino which may be substituted by lower alkyl, or a group of the formula

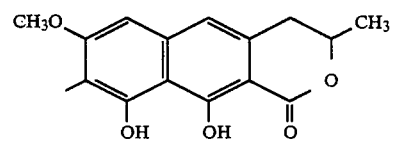

provided that when R' is amino and A' is a group of the formula

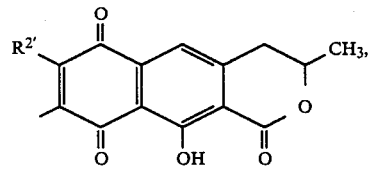

$R^{2'}$ is amino which may be substituted by lower alkyl, and salts thereof.

Referring to the above compounds (I) and (I'), the lower alkoxy represented by R, $R^2$, $R^{2'}$, $R^3$, $R^4$ and $R^5$ is, for example, $C_{1-3}$ alkoxy, such as methoxy, ethoxy or propoxy. The lower alkoxy containing at least 2 carbon atoms as represented by R' is, for example, $C_{2-3}$ alkoxy, such as ethoxy or propoxy.

The amino which may be substituted by lower alkyl represented by R, $R^1$, $R^2$ and $R^{2'}$, is for example, unsubstituted amino or amino substituted by $C_{1-3}$ alkyl, such as methylamino, ethylamino or propylamino.

As for $R^4$ and $R^5$, wherein both are hydrogen are preferable.

The compound (I) wherein R and $R^2$ are each $C_{1-3}$ alkoxy or amino which may be substituted by $C_{1-3}$ alkyl and $R^1$ and $R^3$ are each hydrogen is preferable.

The compounds (I) and (I'), wherein R (or R') and $R^2$ (or $R^{2\prime}$), if present, is amino which may be substituted by $C_{1-3}$ alkyl is more preferable.

The compounds represented by the general formula (I) include, for example, the following compounds:

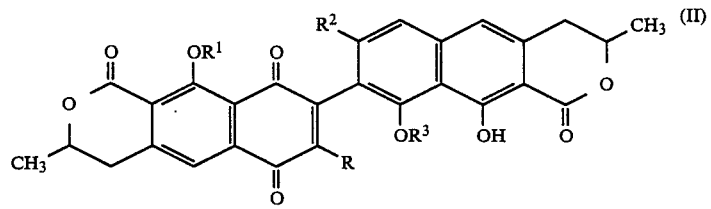

| Compound No. | R | $R^1$ | $R^2$ | $R^3$ |
|---|---|---|---|---|
| 1 | $OCH_3$ | H | $OCH_3$ | H |
| 2 | $OCH_3$ | H | OH | H |
| 3 | OH | H | OH | H |
| 4 | $NH_2$ | H | OH | H |
| 6 | $NH_2$ | H | $NH_2$ | H |
| 8 | $OC_2H_5$ | H | $OCH_3$ | H |
| 9 | $OC_2H_5$ | H | $OC_2H_5$ | H |
| 10 | $OC_2H_5$ | H | OH | H |
| 11 | $NHCH_3$ | H | $NHCH_3$ | H |
| 12 | $NHCH_3$ | H | $NHCH_3$ | H |
| (isomer of compound 11) | | | | |
| 13 | $OCH_3$ | $CH_3$ | $OCH_3$ | $CH_3$ |
| 14 | $OCH_3$ | H | — | — |

(A in compound (I) is hydrogen)

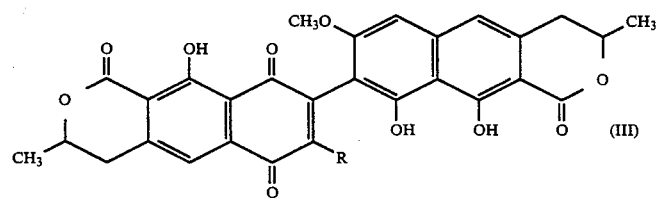

R = $OCH_3$ : compound 5
R = $NH_2$ : compound 7
R = $NHCH_3$: compound 15

Among the compounds shown above, the compounds 1, 2, 3, 4 and 5 are called xanthomegnin, monodemethylxanthomegnin, luteosporin, plastatin and viomellein, respectively, and have been isolated as fungal metabolites or chemical modifications thereof [cf. Chem Ber., 112, 95714 978 (1979) and J. Antibiotics, 38, 706–712 (1985)].

Compounds 13 and 14 are disclosed in J. Chem. Soc. Perkin I, 163 (1975) and Chem. Ber., 112, 957 (1979), respectively.

The above-mentioned compounds of the formula (I') are novel substances.

The compounds (I) can be obtained as microbial products or chemical modifications thereof.

Any of those microorganisms which belong to the genus Penicillium and are capable of producing the compound 1, 2 or 5 may be used in the practice of the invention. An example is the fungal strain No. 8354 isolated from a soil sample collected in Burma and having the following mycological properties:

Growth on various media
(1) Malt extract-agar medium
The growth is luxuriant and, after 2 weeks of growth at 28° C., colonies have a diameter of 8–9 cm. The colony surface consists of a slightly raised velvety mycelial mass. The periphery is rather thin with a regular marare very good. The growth is yellowish white to white in the middle, dark greenish gray to gray in the surrounding zone, and light yellowish white on the margin. The reverse side is reddish brown in the middle, and yellowish brown to light yellow in the periphery. Good growth occurs in the pH range of 3–9. The temperature range for growth is 12–39° C., and the optimum temperature range is 17–35° C.

(2) Potato-glucose-agar medium
The growth is luxuriant and, after 2 weeks of growth at 28° C., colonies have a diameter of 8–9 cm. The surface consists of a slightly raised velvety mycelial mass, and the central portion is uneven. The periphery is rather thin, the margin being regular. Water droplets are found on the mycelial mass. Growth of aerial hyphae and formation of conidia are very good. The growth is reddish purple to white in the middle, dark greenish gray in the surrounding zone, and light reddish brown on the margin. Sectoring occurs in rare cases. The reverse side is dark red to reddish brown. A soluble reddish purple pigment is formed.

(3) Czapek agar medium
The growth is moderate and, after 2 weeks of growth at 28° C., colonies have a diameter of 6–7 cm. The surface consists of a slightly raised velvety mycelial mass, with the middle portion more raised. The periphery is rather thin and has a regular margin. Growth of aerial hyphae and formation of conidia are moderate. The growth is light reddish purple to white in the middle, gray in the surrounding zone, and ocher to white on the margin. The reverse side is dark reddish brown to reddish brown in the middle, and ocher to yellowish white in the surrounding area The growth is luxuriant and, after 2 weeks of growth at 28° C., the colony diameter amounts to 8–9 cm. The surface consists of a velvety mycelial mass not much raised but extending laterally, with the middle portion raised irregularly and the periphery margined regularly. Growth of aerial hyphae and formation of conidia are very good. The growth is reddish purple to yellowish white in the middle, dark greenish gray to gray in the surrounding zone, and yellowish white on the margin. The reverse side is reddish purple in the middle, and dark yellowish brown to light yellow in the surrounding area. Morphology of the microorganism Conidiophore: 30–100 μm, branching somewhat irregular.

Penicillus: Biverticillate, with "obpyriform" phialides (Asymmetrica).

Phialide: 1–1.5 μm×6–8 μm, slightly tapering. Four to six phialides form a verticil or whorl.

Conidium: Ellipsoidal to subglobose, 1.5–2μm.

From comparison of the above characteristics with the data described in the Japanese edition of D. Malloch's "Isolation, Culture and Identification of Fungi", translated by Shun-ichi Udagawa, published by Ishiyaku Shuppan, 1983, page 51, Identification Key Table, it is evident that the above strain belongs to the genus Penicillium. Furthermore, from comparison with the characteristics of Penicillium fungi as described in K. B. Raper et al.: "Manual of the Penicillia", The Williams & Wilkins Company, 1949, said strain was found to belong to Asymmetrica, and, based on the findings, such as good branching of penicilli and no perithecium formation as well as on the states of hyphae and conidiophores on colonies, among others, the strain was considered to be identifiable as *Penicillium janthinellum* and accordingly was named *Penicillium janthinellum* No. 8354.

The above-mentioned *Penicillium janthinellum* No. 8354 strain has been deposited, since Apr. 7, 1988, with the Institute for Fermentation, Osaka (IFO) under the deposit number IFO-32075 and, since Apr. 14, 1988, with the Fermentation Research Institute (FRI), Agency of Industrial Science and Technology, Ministry of International Trade and Industry, Japan (1-3 Higashi 1-chome, Tsukuba City, Ibaraki Prefecture, Japan) under the deposit number FERM BP-1852 under the Budapest Treaty.

Strains of the genus Penicillium are subject to spontaneous or induced mutation, as microorganisms in general are. Thus, a large number of mutants obtained by various means, for example, irradiation with X rays, gamma rays, ultraviolet rays or the like radiations, monospore separation, treatment with various agents or cultivation on various agent-containing media as well as mutants resulting from spontaneous mutation can be used in the practice of the invention if they can produce the compound 1, 2 and/or 5.

The medium to be used in cultivating such microorganisms as mentioned above may be either liquid or solid provided that it contains nutrient sources utilizable by the strain used. In large-scale cultivation, however, the use of a liquid medium is more suitable. The medium contains one or more assimilable carbon sources, one or more digestible nitrogen sources, one or more inorganics and one or more trace nutrients, as necessary. Usable as carbon sources are, for example, glucose, lactose, sucrose, maltose, dextrin, starch, glycerin, mannitol, sorbitol, fats and oils (e.g. soybean oil, olive oil, rice bran oil, sesame oil, lard, chicken oil) and various fatty acids (e.g. lauric acid, myristic acid, palmitic acid, stearic acid, oleic acid). Usable as nitrogen sources are, for example, meat extract, yeast extract, dried yeasts, soybean flour, corn steep liquor, peptone, cotton seed flour, molasses, urea, and ammonium salts (e.g. ammonium sulfate, ammonium chloride, ammonium nitrate, ammonium acetate). Furthermore, salts, for example salts containing sodium, potassium, calcium, magnesium, etc., salts of such metals as iron, manganese, zinc, cobalt and nickel, salts of phosphoric acid, salts of boric acid and salts of organic acids such as acetic acid and propionic acid, are used, as necessary. The medium may further contain amino acids (e.g. glutamic acid, aspartic acid, alanine, lysine, valine, methionine, proline), peptides (e.g. dipeptides, tripeptides), vitamins (e.g. $B_1$, $B_2$, nicotinic acid, $B_{12}$, C.), nucleic acids (e.g. purine, pyrimidine, derivatives thereof) and so on. For adjusting the pH of the medium, an inorganic or organic acid, an alkali, a buffer agent or the like is of course added and, for defoaming, an appropriate amount of a fat or oil, a surfactant or the like is added.

The means of cultivation may be stationary culture, shake culture or culture with aeration and agitation, for instance. It goes without saying that the so-called submerged culture with aeration and agitation is desirable for large-scale production. The cultivation conditions of course may vary depending on the state and composition of medium, the kind of microorganism, the means of cultivation and other factors. Generally, however, a temperature of about 15° C. to 37° C. and an initial pH of about 3 to 10 should recommendably be used. In particular, the temperature in the middle stage of cultivation should desirably be about 20° C. to 32° C., and the initial pH about 4 to 6. The required cultivation period may vary also depending on the conditions mentioned above. It is recommendable that the cultivation should be conducted until the physiologically active substance concentration becomes maximal. Generally, the time required therefor is about 2 to 14 days in the case of shake culture or culture with aeration and agitation in a liquid medium.

The compounds 1, 2 and 5 thus produced are present in the culture filtrate and in the cells and therefore may be purified from the supernatant as well as from the cells following separation of the culture into the supernatant and cells by centrifugation or filtration but, more advantageously, can be purified directly from the culture following addition of an organic solvent, such as methanol, to the culture.

The compounds 1, 2 and 5, which are neutral or acidic liposoluble substances, are recovered from the culture by suitably applying conventional means of separation and purification for recovering such neutral or acidic liposoluble microbial metabolites. Thus, for instance, techniques utilizing solubility differences from impurities, adsorption chromatographic techniques using various carriers, such as active carbon, nonionic high-porosity resins, silica gel and alumina, and other techniques are used either singly or in combination.

The compounds 1, 2 and 5 produced in the culture may be recovered by first separating the culture into the cell fraction and culture supernatant fraction by filtration or the like means and then extracting both the fractions with an organic solvent or by adding directly to the culture an organic solvent, for example an organic solvent capable of dissolving the compounds 1, 2 and 5, such as methanol, acetone or ethyl acetate, followed by stirring for extraction of said compounds.

As the organic solvent to be used in extraction of said compounds from the culture, culture filtrate or cells, there may be mentioned, for example, fatty acid esters, such as ethyl acetate, alcohols, such as butanol, halogenated hydrocarbons, such as chloroform, and ketones, such as acetone. The compounds 1, 2 and 5 are purified from the extract containing them by concentration of the extract, adsorption on an adsorbent carrier, such as silica gel, and development with an appropriate solvent. Depending on the content and content ratio, one of said compounds alone may precipitate out and, in that case, the compound can be purified by recrystallization.

When, for example, silica gel (e.g. Merck's Kieselgel), preferably pretreated with oxalic acid, is used as the adsorbent, a combination of a polar organic solvent and a nonpolar one, for example a mixed solvent system composed of methanol and chloroform or of methylene chloride or ethyl acetate and n-hexane, is generally used as the developing solvent. Thus, development is first effected with the nonpolar solvent, followed by the subsequent elution while increasing the proportion of the more polar solvent, whereby the desired product or products can be separated from impurities.

When the impurity content is high, the compounds 1, 2 and 5 can be obtained by repeating the chromatographic procedure with different combinations of such organic solvents.

Thus, the culture is made acidic and extracted with an organic solvent immiscible with water, such as ethyl acetate, the extract is filtered through a filtration aid, such as Hyflo-Super-Cel, and the organic layer separated from the filtrate is washed with water and concentrated, whereby a precipitate forms.

The precipitate is collected by filtration and recrystallized from a mixed solvent such as chloroform-methanol to give the compound 1 as crystals. The mother liquor is concentrated, n-hexane is added to the concentrate, the resultant crude powder is subjected to column chromatography using silica gel (Merck) pretreated with oxalic acid, followed by development with chloroform and chloroform-methanol (20:1). The fractions 1 and 2, each giving a single spot in thin layer chromatography, are washed with water and then concentrated to give the compounds 1 and 2, respectively, each as crystals. Concentration of another mixture fraction gives a crude powder, which is applied again to a silica gel column pretreated with oxalic acid. Development is carried out with chloroform, and the single-spot fraction is washed with water and concentrated to give the compound 5 as crystals. Treatment of compound 1 with an inorganic acid or a Lewis acid gives the compounds 2 and 3.

These microbial metabolites and the naphthopyran compounds (i) derived therefrom, which have a quinone structure, can be converted to the hydroquinone-form compounds by treatment with a reducing agent such as $Na_2S_2O_4$.

The chemical conversion of the natural substances can be effected, for example in the following manner.

(1) Treatment of compounds 1, 2 or 5 in an organic solvent with $NH_3$ gives the corresponding compound 6, 4 or 7, respectively.

As the organic solvent to be used in conducting the reaction, there may be mentioned organic solvents inert to reaction, there the reaction, for example alcohols, such as methanol and ethanol, halogenated hydrocarbons, such as chloroform and dichloromethane, and ethers, such as diethyl ether. The reaction may be carried out at a temperature of $-40°$ C. to $=40°$ C. and, in most cases, it is conducted at 0° C. to 30° C.

The reagent is used in an amount which varies depending on the starting material but usually in an amount of 1 to 1,000 moles per mole of the starting material, in most cases in an excess amount of 20 to 200 moles per mole of the starting material. The reaction period also may vary depending on the kind of starting material. In cases where the reactivity is high, the reaction will be complete within 10 minutes whereas, in some instances where the compound used has low reactivity, 2 days or more may be required.

(2) Treatment of the compound 2 or 3 with an 1-alkyl3-aryltriazene in an organic solvent gives the compounds 8 and 9 or the compound 10, respectively.

The 1-alkyl-3-aryltriazene to be used in the above reaction is, for example, 1-methyl-3-p-tolyltriazene, 1-ethyl-3-p-tolyltriazene, 1-benzyl-3-p-tolyltriazene (p-$CH_3C_6H_4N=NNH-CH_2C_6H_5$), 3-(2-hydroxyethyl)-1-phenyltriazene or 3-(3-hydroxypropyl)-1-phenyltriazene.

As the organic solvent to be used in carrying out the reaction, there may be mentioned those organic solvents which will not interfere with the reaction, for example halogenated hydrocarbons, such as dichloromethane and chloroform, and ethers, such as diethyl ether. The reaction temperature is generally $-20°$ C. to 60° C., in most cases 0° C. to 30° C. The reagent is used in an amount which varies depending on the kind of starting material and the kind of said reagent. Generally, however, the reagent 1-alkyl-3-aryltriazene is used in an amount of 1 to 50 moles, mostly 1.2 to 5 moles, per mole of the starting material. In cases where the reactivity is high, the reaction period required is not longer than 5 minutes whereas, in certain cases where the reaction proceeds slow, 2 days or longer may be required.

(3) Treatment of the compounds 1 and 5 with monomethylamine in an organic solvent in the presence or absence of an basic catalyst give Compounds 11 (and 12) and 15, respectively.

The basic catalyst to be used in the above reaction is, for example, organic amines (e.g. triethylamine, pyridine) and inorganic bases (e.g. sodium hydroxide, potassium carbonate).

As the organic solvent to be used in carrying out the reaction, there may be mentioned those organic solvents which will not interfere with the reaction, for example halogenated hydrocarbons, such as dichloromethane and chloroform, and ethers, such as diethyl ether. The reaction temperature is generally $-20°$ C. to 60° C., in most cases 0 C. to 30° C. The reagent is used in an amount which varies depending on the kind of starting material and the kind of said reagent. Generally, however, the reagent lower alkylamine such as monoethylamine is used in an amount of 1 to 50 moles, mostly 1.2 to 5 moles, per mole of the starting material. In cases where the reactivity is high, the reaction period required is not longer than 5 minutes whereas, in certain cases where the reaction proceeds slow, 2 days or longer may be required.

The compounds (I) form inorganic salts with alkali metals, such as sodium and potassium, when desired and, therefore, may be isolated in the form of physiologically acceptable salts.

The following test examples will illustrate the human placental aromatase inhibiting activity in vitro and estrogen synthesis inhibiting activity in rats of the compounds (I) in further detail.

Test Example 1 In vitro aromatase inhibiting activity

Preparation of human placental microsome:

The method of F. A. Thompson et al. [Journal of Biological Chemistry, 249, 5364 (1974)] was partly modified. Thus, a placenta was washed with cooled 0.15 M KCl and, after removal of adhering membranes and great blood vessels, minced to sufficiently small pieces by means of scissors. To the minced tissue was added cold 0.02 M phosphate buffer (pH 7.4) containing 0.25 M sucrose in an amount of 1 ml per 1 g of tissue, the mixture was homogenized with a Polytron homogenizer (30 seconds, three times, in ice) and then centrifuged at 800×g for 10 minutes, the supernatant was subjected to centrifugation at 20,000×g for 30 minutes, followed by further centrifugation at 148,000×g for 45 minutes, and the pellet thus obtained was used as a microsome fraction. The microsome obtained was suspended in the same phosphate buffer as mentioned above in a concentration corresponding to 10 g of wet placenta per ml. The suspension was stored at −80° C. and, just prior to use, diluted 5 to 6 times.

Aromatase activity measurement and inhibitory activity:

The method of F. A. Thompson et al. (vide supra) was partly modified as follows:

A reaction solution (225 μl) containing 4 μM 4-androstene-3,17-dione, 140,000 dpm, 1,2[$^3$H]-androstenedione, 550 μM NADPH, 20 μl of the above microsome and 5 μl of buffer or 5 μl of an inhibitor-containing solution was incubated at 37° C. for 1 hour. In this measurement system, aromatization of androstenedione gives [$^3$H]—H$_2$O. Therefore, this reaction mixture was extracted with 0.5 ml of chloroform for separation, the aqueous layer obtained was treated with 0.25 ml of 5% active carbon for removal of free steriods and then subjected to low speed centrifugation. A scintillator (3 ml) was added to 0.2 ml of the supernatant, and the radioactivity was measured by means of a liquid scintillation counter. The percent inhibition (%) was determined by comparing the result thus obtained with the result for a control sample as obtained without adding any inhibitor. The activity was expressed in terms of IC$_{50}$ (μg/ml), namely the inhibitor concentration required for 50% inhibition of the enzyme activity at the substrate (androstenedione) concentration of 4 μM.

TABLE 1

Test Example 2 Estrogen synthesis inhibition in rats

| Compound | Human placental aromatase inhibiting activity IC$_{50}$ (μg/ml) |
|---|---|
| 1 | 4.7 |
| 2 | 13.5 |
| 3 | 73.0 |
| 4 | 16.5 |
| 5 | 73.0 |
| 6 | 3.9 |
| 7 | 27.5 |
| 8 | 16.9 |
| 9 | 24.5 |
| 10 | 29.4 |
| 11 | 250.0 |
| 12 | 6.0 |
| 13 | 10.2 |
| 14 | 0.8 |

The compounds (I) were examined for in vitro estrogen synthesis inhibiting activity in the following test example.

Groups of five young SD rats (male, 19 days old) were used. Test groups were administered subcutaneously with the test compounds suspended in 0.2% gum arabic-containing physiological saline in a dose of 25 mg/kg or 50 mg/kg at 24-hour intervals for consecutive 4 days. Non-test groups (control groups 1 and 1) were administered with 0.2 ml of 0.2% gum arabic-containing physiological saline. On the third day after initiation of the test, a single dose of pregnant mare serum gonadotropin (PMSG) was administered subcutaneously in a dose of 10 U/rat to the test groups and to the control group 2, following the administration of the test compounds. On the fifth day, blood samples were collected from the inferior aorta under ether anesthesia by means of a heparin-containing blood sampling syringe and subjected to centrifugation. The plasma samples thus obtained were subjected to plasma estradiol-17B level determination by radioimmunoassay. The uterus and ovaries were excised from each rat and, after removal of superfluous connective tissues, weighed. The results thus obtained are shown in Table 2. 4-Hydroxyandrostenedione (4-OHA) was used as a reference compound for the pharmacological effect evaluation.

TABLE 2

| Compound | Dose (mg/kg/day) | Body weight gain (g) | Tissue weight Uterus (mg) | Tissue weight Ovaries (mg) | Plasma estradiol-17β level (pg/ml) |
|---|---|---|---|---|---|
| Test I | | | | | |
| Control group 1 | — | 22.6 ± 2.1 | 26.3 ± 7.3 | 11.4 ± 1.7 | 26.0 ± 19.8 |
| Control group 2 (PMSG) | — | 23.8 ± 2.6 | 97.8 ± 10.3 | 32.8 ± 4.4 | 568.6 ± 69.7 |
| 4-OHA | 100 | 25.0 ± 1.6 | 60.6 ± 9.0**** | 24.3 ± 4.5** | 115.5 ± 47.4**** |
| 1 | 25 | 22.4 ± 3.1 | 88.9 ± 9.0 | 23.7 ± 3.4*** | 204.7 ± 67.0**** |
| | 50 | 21.4 ± 2.7 | 91.9 ± 14.4 | 25.5 ± 5.5 | 250.9 ± 161.1 |
| 6 | 25 | 23.0 ± 3.5 | 102.2 ± 15.5 | 32.2 ± 7.0 | 353.2 ± 48.4 |
| | 50 | 24.6 ± 0.9 | 103.1 ± 11.6 | 32.0 ± 2.9 | 326.0 ± 115.1**** |
| 7 | 25 | 22.8 ± 0.4 | 94.1 ± 5.5 | 31.2 ± 8.5 | 323.4 ± 161.2** |
| | 50 | 23.6 ± 0.9 | 110.0 ± 14.9 | 27.7 ± 2.7 | 206.3 ± 54.8**** |
| Test II | | | | | |
| Control group 1 | — | 19.6 ± 3.0 | 23.8 ± 2.7 | 15.5 ± 3.2 | 8.9 ± 6.1 |
| Control group 2 (PMSG) | — | 20.6 ± 3.4 | 80.8 ± 11.6 | 31.5 ± 4.0 | 240.0 ± 34.9 |

TABLE 2-continued

| Compound | Dose (mg/kg/day) | Body weight gain (g) | Tissue weight Uterus (mg) | Ovaries (mg) | Plasma estradiol-17β level (pg/ml) |
|---|---|---|---|---|---|
| 4-OHA | 100 | 22.8 ± 1.5 | 61.5 ± 8.2** | 22.3 ± 3.3*** | 36.1 ± 33.0**** |
| 3 | 25 | 18.2 ± 2.2 | 93.6 ± 22.4 | 21.3 ± 4.4*** | 124.1 ± 53.3*** |
|   | 50 | 19.4 ± 1.8 | 115.4 ± 30.4 | 22.6 ± 5.4** | 71.1 ± 23.4**** |
| 4 | 25 | 21.0 ± 1.6 | 97.4 ± 17.8 | 20.8 ± 3.9*** | 156.0 ± 47.8** |
|   | 50 | 17.0 ± 3.3 | 86.6 ± 9.6 | 26.8 ± 4.8 | 190.3 ± 19.9* |
| 5 | 25 | 22.8 ± 1.8 | 104.6 ± 16.6 | 25.3 ± 4.9 | 60.5 ± 51.1**** |
|   | 50 | 22.0 ± 1.2 | 97.7 ± 16.0 | 21.0 ± 2.5 | 63.8 ± 24.3**** |
| Test III |   |   |   |   |   |
| Control group 1 | — | 22.4 ± 1.1 | 25.4 ± 2.7 | 14.9 ± 1.6 | 2.7 ± 1.6 |
| Control group 2 (PMSG) | — | 22.2 ± 1.1 | 100.2 ± 20.8 | 34.7 ± 6.6 | 327.9 ± 126.6 |
| 4-OHA | 100 | 24.8 ± 0.8 | 71.9 ± 8.6* | 26.3 ± 1.7 | 52.3 ± 21.7** |
| 2 | 25 | 23.2 ± 1.5 | 115.7 ± 14.0 | 29.4 ± 7.5 | 189.5 ± 123.4 |
|   | 50 | 21.6 ± 0.5 | 106.3 ± 14.0 | 29.0 ± 2.5 | 195.1 ± 79.3 |

(Mean ± SD)
(Student' t-test)
*$P < 0.05$, $P < 0.02$, *$P < 0.01$, ****$<0.001$ against PMSG group All the compounds tested significantly suppressed the blood estrogen level increase by stimulation by PMSG administration.

The compounds (I) thus have potent aromatase inhibiting activity and can be used advantageously in the prevention or treatment of estrogen-dependent diseases, such as breast cancer, endometriosis, carcinoma of uterine body and benign mastosis, and in conception control in mammals (horse, cattle, swine, rat, human, etc.). The compounds (I) have low toxicity.

The compounds (I) are administered orally, nonorally by injection, or locally by application to the skin, mucosa, vagina, rectum, etc.

The dose of compounds (I) may vary depending on the target disease and route of administration. In treating breast cancer, for instance, the compounds are administered to human adults orally or non-orally in a daily dose of 0.01 to 200 mg/kg, in particular 0.1 to 20 mg/kg.

For oral administration, the compounds (I) are used in the form of capsules, tablets, granular compositions, syrups, powders and the like, which may additionally contain additives, such as excipients, binders, disintegrants, lubricants, coloring agents, flavors and stabilizers.

Among such additives, there may be mentioned starch, sucrose, fructose, lactose, glucose, mannitol, sorbitol, precipitated calcium carbonate, crystalline cellulose, carboxyethylcellulose, dextrin, gelatin, gum arabic, magnesium stearate, talc and hydroxypropylmethylcellulose.

For non-oral or parenteral administration, the active ingredients can be dissolved or suspended in conventional diluents (aqueous or non-aqueous carriers). The diluents include, among others, physiological saline, Ringer's solution, aqueous glucose solution, alcohol, glycols, glycerin, fatty acid glycerides, plant- or animal-derived oils, and paraffins. The pharmaceutical compositions may further contain, as additives, emulsifiers, suspending agents, solubilizing agents, stabilizers, preservatives, soothing agents, tonicity agents, buffers, pH adjusting agents, coloring agents, coating agents and so forth. The pharmaceutical compositions or dosage forms can be produced in the conventional manner.

EXAMPLES

The following examples are further illustrative of the present invention. In the examples, the "percent (%)" used in reference to medium compositions is "weight by volume percent".

Example 1

A culture of the No. 8354 strain of *Penicillium janthinellum* as grown to a sufficient extent on a slant lanthine yeast-malt-agar medium was inoculated into a 2-liter Sakaguchi flask containing 500 ml of a sterilized seed culture medium containing 2% glucose, 3% maltose, 1.5% raw soybean meal, 1% corn steep liquor, 0.5% polypeptone, 0.3% yeast extract and 0.3% sodium chloride, pH 6.0, and cultured on a reciprocating shaker at 28° C. for 2 days. A 400-ml portion of the culture broth was transferred to a 50-liter fermenter containing 30 liter of the same sterilized seed culture medium as mentioned above with 0.05% Actocol (antifoam manufactured by Takeda Chemical Industries) added thereto, and cultivation was carried out with aeration and agitation at 28° C. for 2 days. A 5-liter portion of the culture broth thus obtained was transferred to a 200-liter fermenter containing 100 liters of a sterilized production medium containing 1% glucose, 4% dextrin, 0.5% soybean meal, 0.5% polypeptone, 0.2% malt extract, 0.1% potassium dihydrogen phosphate, 0.05% manganese sulfate, 0.05% ferrous sulfate, 0.05% magnesium sulfate, 0.5% precipitated calcium carbonate and 0.05% Actocol, pH 7.5, and cultivation was carried out for 90 hours under the following conditions: temperature 28° C, inside pressure 1.0 kg/cm², aeration 100 liters/min, and agitation 150 rpm.

Example 2

The culture broth (85 liters) obtained in Example 1 was adjusted to pH 2.7, ethyl acetate (85 liters) was added, and the mixture was stirred for 30 minutes and then filtered with Hyflo-Super-Cel (Johns-Manville) as a filter aid. Of the filtrate, the ethyl acetate layer (80 liters) was washed with water and concentrated under reduced pressure. The resultant precipitate was collected by filtration and crystallized from chloroform-methanol to give the compound 1 as orange-colored crystals (12.3 g). The mother liquor, after separation of the precipitate, was concentrated, n-hexane was added, and the crude powder (14.1 g) thus obtained was dissolved in chloroform and applied to a column of silica gel (500 g, Merck) treated with oxalic acid in advance. Development was carried out with chloroform (4 liters) and chloroform-methanol (20:1) (2 liters), the eluate being collected in 50-ml portions. The fraction No. 9 was washed with water, dried and concentrated, the residue thus obtained was crystallized from chloroform-methanol to give a second crop (1.70 g) of the compound 1 as crystals. The fraction No. 11 was treated in the same manner to give 301 mg of the compound 2 as orange-colored crystals. The fraction No. 8 was washed with water, dried and concentrated, and the crude powder (5.25 g) thus obtained was dissolved in a small amount of chloroform and applied to a silica gel column (250 g) pretreated with oxalic acid. Development was carried out with chloroform (2.5 liters) and the eluate was collected in 100-ml portions. The fractions Nos. 13–17 were combined, washed with water, dried and concentrated. Crystallization of the residue thus obtained from chloroform-methanol gave the compound 5 as orange-colored crystals (1.29 g). Compound 1: Melting point above 270° C.

Elemental analysis:
Calculated for $C_{30}H_{22}O_{12} \cdot 1/2H_2O$:
C, 61.64; H, 3.78.
Found: C, 61.64; H, 3.78.
Mass analysis (FDMS): m/z 574 (M+).

. Compound 2: Melting point above 270° C.

Elemental analysis:
Calculated for $C_{29}H_{20}O_{12}$:
C, 62.15; H, 3.60;
Found: C, 61.96; H, 3.53.

Compound 5: Melting point above 270° C.

Elemental analysis:
Calculated for $C_{30}H_{24}O_{11} \cdot 1/2H_2O$:
C, 63.27; H, 4.42;
Found: C, 63.71; H, 4.19.
Mass analysis (EIMS): m/z 560 (M+).

Example 3

The compound 1 (5.0 g) was dissolved in a mixture of chloroform (250 ml) and acetic acid (100 ml), then 47% hydrobromic acid (aqueous) was added dropwise, and the resultant mixture was stirred at room temperature. After 30 hours, water (250 ml) was added to the reaction mixture, and the resultant precipitate was collected by filtration, washed with water and crystallized from acetone to give the compound 3 (386 mg) as orange-colored crystals. The mother liquor chloroform layer was washed with water, dried and concentrated, the crude powder (4.2 g) thus obtained was dissolved in a small amount of chloroform and applied to a silica gel column (150 g) pretreated with oxalic acid. Development was carried out with chloroform (1.2 liters) and chloroform-methanol (40:1, 1.2 liters) and the eluate was collected in 200-ml portions. The fractions Nos. 4 and 5 were combined, washed with water, dried and concentrated, and the residue was crystallized from chloroform-methanol, whereby the compound 1 (starting material) was recovered as crystals (2.29 g). The fractions Nos. 7 and 8 were combined and treated in the same manner to give the compound 2 as crystals (1.48 g). Furthermore, the fractions Nos. 9 and 10 were combined and treated in the same manner. Crystallization from acetone gave the compound 3 as crystals (203 mg).

Compound 3: Melting point above 225° C.

Elemental analysis:
Calculated for $C_{28}H^{18}O_{12} \cdot 1/2H_2O$:
C, 60.55; H, 3.45;
Found: C, 60.87; H, 3.27.
Mass analysis (EIMS): m/z 546 (M+).

Example 4

The compound 2 (1.0 g) was dissolved in chloroform (200 ml), then 4.7% ammonia-methanol (10 ml) was added, and the mixture was stirred at room temperature for 2 hours. Thereafter, the reaction mixture was concentrated to dryness, the residue was suspended in chloroform (500 ml), and the suspension was washed with 0.2 N hydrochloric acid (300 ml) and water (300 ml) in that order and concentrated to give the compound 4 as red crystals (903 mg). Compound 4: Melting point above 230° C.

Elemental analysis:
Calculated for $C_{28}H_{19}NO_{11}$:
C, 61.66; H, 3.51; N, 2.57;
Found: C, 61.49; H, 3.49; N, 2.32.
Mass analysis (FDMS): m/z 545 (M+).

Example 5

The compound 1 (1.50 g) was dissolved in chloroform (150 ml), then 4.7% ammonia-methanol (15 ml) was added, and the mixture was stirred at room temperature. After an hour, the reaction mixture was concentrated and applied to a silica gel column (100 g) pretreated with oxalic acid. The column was washed with chloroform (800 ml) and then development was carried out with chloroform-methanol (10:1, 800 ml) and chloroform-methanol (5:1, 800 ml) in that order, the eluate being collected in 200-ml portions. The fractions Nos. 2–6 were combined, washed with water and concentrated to give the compound 6 as red crystals (1.29 g).

Compound 6: Melting point above 245° C.

Elemental analysis:
Calculated for $C_{28}H_{20}N_2O_{10} \cdot 1/2H_2O$:
C, 60.76; H, 3.82; N, 5.06;
Found: C, 60.98; H, 3.68; N, 5.02.
Mass analysis (FDMS): m/z 544 (M+).

Example 6

The compound 5 (2.0 g) was dissolved in chloroform (200 ml), then 4.7% ammonia-methanol (20 ml) was added, and the mixture was stirred at room temperature. After 24 hours, the reaction mixture was concentrated, the residue was suspended in chloroform (200 ml) and the suspension was washed with 0.2 N hydrochloric acid (100 ml) and then with water (100 ml), again concentrated, and subjected to column chromatography using silica gel (100 g) pretreated with oxalic acid. Development was carried out with chloroform (2 liters) and the eluate was collected in 200-ml portions. The fractions Nos. 4 and 5 were combined, washed with water, dried and concentrated, and the residue was crystallized from chloroform-methanol to give the compound 7 as red crystals (733 mg).

Compound 7: Melting point above 270° C.

Elemental analysis:
Calculated for $C_{29}H_{23}NO_{10}$:

C, 63.85; H, 4.25; N, 2.57;
Found: C, 64.05; H. 4.22; N, 2.48.
Mass analysis (FDMS): m/z 545 (M+).

Example 7

The compound 2 (50 mg) was dissolved in chloroform (5 ml), then 1-ethyl-3-p-tolyltriazene (22 mg) was added, and the mixture was stirred at room temperature. After 30 minutes, the reaction mixture was washed twice with 1 N hydrochloric acid (5 ml) and then twice with water (5 ml), dried and concentrated. The residue obtained was subjected to column chromatography on silica gel (5 g) pretreated with oxalic acid. Development was carried out with chloroform (15 ml) and chloroform-methanol (40:1, 15 ml), the eluate being collected in 3-ml portions. The fractions Nos. 5–8 were combined, washed with water, dried and concentrated, and the residue was crystallized from chloroform-methanol to give the compound 8 as orange-colored crystals (37 mg).

Compound 8: Melting point above 270° C.

Elemental analysis:
Calculated for $C_{31}H_{24}O_{12} \cdot 1/2H_2O$
C, 62.31; H, 4.22;
Found: C, 62.52; H, 3.92.

Example 8

The compound 3 (50 mg) was dissolved in chloroform (5 ml), then 1-ethyl-3-p-tolyltriazene (45 mg) was added, and the mixture was stirred at room temperature for 30 minutes. The reaction mixture was washed twice with 1 N hydrochloric acid (5 ml) and twice with water (5 ml), dried over anhydrous sodium sulfate and concentrated, and the residue was subjected to column chromatography on silica gel (5 g) pretreated with oxalic acid. Development was carried out with chloroform (30 ml) and the eluate was collected in 3-ml portions. The fractions Nos. 6–8 were combined, washed with water, dried and concentrated to dryness. Crystallization of the residue from chloroform methanol methanol gave the compound 9 as orange-colored crystals (26 mg).

Compound 9: Melting point above 270° C.

Elemental analysis:
Calculated for $C_{32}H_{26}O_{12} \cdot 1/2H_2O$:
C, 62.85; H, 4.45;
Found: C, 63.05; H, 4.34.

Example 9

The compound 3 (100 mg) was dissolved in chloroform (10 ml), 1-ethyl-3-p-tolyltriazene (33 mg, 1.1 equivalents) was added in the same manner as in Example 8, and the mixture was stirred at room temperature for 30 minutes. The reaction mixture was washed once with 1 N hydrochloric acid (5 ml) and twice with water, then dried over anhydrous sodium sulfate, and concentrated. The residue was subjected to column chromatography on silica gel (5 g) pretreated with oxalic acid. Development was carried out with chloroform (40 ml) and chloroform-methanol (40:1, 40 ml) and the eluate was collected in 5-ml portions. The eluate fractions Nos. 7–10 were combined, washed with water, dried and concentrated, and the residue was treated with ether to give the compound 10 as an orange-colored powder (35 mg).

Elemental analysis:
Calculated for $C_{30}H_{22}O_{12} \cdot H_2O$:
C, 60.81; H, 4.08;
Found: C, 60.77; H, 3.87.

Example 10

The compound 1 (200 mg) was dissolved in chloroform (200 ml), then monomethylamine chloride (116 mg) and triethylamine (0.24 ml) were added, and the mixture was stirred at room temperature for 1.5 hours. Thereafter, the reaction mixture was washed with 0.5N hydrochloric acid (10 ml), dried over anhydrous sodium sulfate and concentrated. The resulting residue was purified by applying several times to a silica gel column chromatogrphy pretreated with oxalic acid (developing solvent: chloroform), and then to a thin layer chromatography (silica gel plate pretreated with oxalic acid: developing solvent; chloroform-methanol (20:1) and collected Rf 0.36 fractions.

The fraction collected was washed with water, dried and concentrated. The residue was crystalized from chloroform-methanol to give the crystals of compound 11 73 mg).

The Rf 0.30 fraction collected was treated as the same manner above to give the red crystals of compound 12 (31 mg).

Further, the mixture of compounds 11 and 12 (55 mg) was recovered from the fractions containing both components.

Compound 11

Elemental analysis:
Calculated for $C_{30}H_{24}N_2O_{10} \cdot 1/2\ H_2O$:
C,61.96; H,4.33; N,4.82
Found:
C,61.67; H,4.17; N,5.18
$^1H$ NMR (300 MHz, $\delta$ in $CDCl_3$):
1.53(6H,d), 2.95(4H,m), 3.06(6H,d),
4.60(2H,m), 6.55(2H,m), 7.43(2H,s),
14.37(2H,s)

Compound 12

Elemental analysis:
Calculated for $C_{30}H_{24}N_2O_{10} \cdot 1/2\ H_2O$:
C,61.96; H,4.33; N,4.82
Found:
C,61.74; H,4.12; N,4.77
$^1H$ NMR (300 MHz, $\delta$ in $CDCl_3$):
1.52(6H,d), 2.99(4H,m), 3.05(6H,d),
4.62(2H,m), 6.49(2H,m), 7.45(2H,s),
14.33(2H,s)

Example 11

The compound 5 (100 mg) was dissolved in chloroform (10 ml), then monomethylamine hydrochloride (35.7 mg) and triethylamine (73.7 μl) were added, and the mixture was stirred at room temperature for 24 hours. Insolubles were removed by filtration, and the residue obtained by the concentration of the filtrate was applied to a silica gel column (10 g) pretreated with oxalic acid (developing solvent, chloroform), and then collected 5 ml-fractions.

Fraction Nos. 7 to 11 were collected, washed with water and concentrated. The resulting residue was crystalized from chloroform-methanol to give the red crystals of compound 15 (57 mg).

Elemental analysis:
Calculated for $C_{30}H_{25}N_2O_{10} \cdot 1/2\ H_2O$:
C,63.38; H,4.61; N,2.46

Found:
C,63.72; H,4.30; N,2.59
$^1$H NMR (300 MHz, δ in CDCl$_3$):
1.54(6H,m), 2.61, 2.62(6H accumulated),
2.99(4H,m), 3.89(3H,s), 4.61(1H,m), 4.78(1H,m),
6.28(1H,m), 6.66(1H,br.s), 6.96(1H,s),
7.44(1H,s), 9.81(1H,s), 13.87(1H,br.), 14.54,
14.55(1H accumulated, each s).

Example 12

Tablets (for 1,000 tablets)

| | |
|---|---|
| Compound 1 | 50 g |
| Lactose | 80 g |
| Corn starch | 46 g |
| Magnesium stearate | 1 g |
| Talc | 3 g |
| | 180 g |

A homogeneous mixture of 50 g of compound 1, 80 g of lactose and 30 g of corn starch was made up into granules in the conventional manner. The granular composition was combined with a powder mixture composed of magnesium stearate and the remaining portion of corn starch, followed further by addition of the talc powder. After uniform admixture, the resultant mixture was tableted into 1,000 tablets in the conventional manner.

The tablets are to be administered orally to adult patients with breast cancer at a daily dose of 1 to 5 tablets depending on the symptom.

What is claimed is:

1. A compound of the formula:

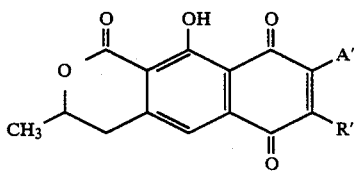

wherein R' is amino which may be substituted by C$_{1-3}$ alkyl and A' is a group of the formula

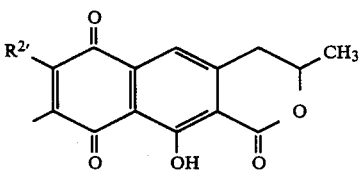

in which R$^{2'}$ is amino which may be substituted by C$_{1-3}$ alkyl, or A' is a group of the formula

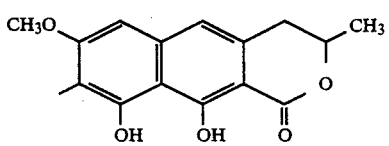

or a physiologically acceptable salt thereof.

2. The compound according to claim 1, wherein R' and R$^{2'}$ are each amino.

3. The compound according to claim 1, wherein R' is amino and A' is the formula:

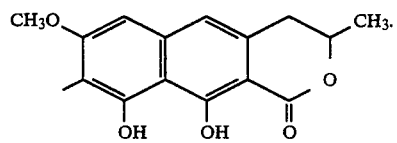

4. A method for prevention or treatment of an estrogen-dependent disease in a mammal, which comprises administering to such a mammal an effective aromatase-inhibiting amount of a compound of the formula

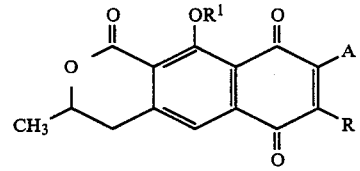

wherein R is hydroxy, lower alkoxy or amino which may be substituted by lower alkyl; R$^1$ is hydrogen or lower alkyl; and
A is hydrogen,
a group of the formula

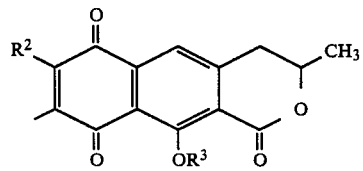

in which R$^2$ is hydroxy, lower alkoxy or amino which may be substituted by lower alkyl and R$^3$ is hydrogen or lower alkyl, or
A is a group of the formula

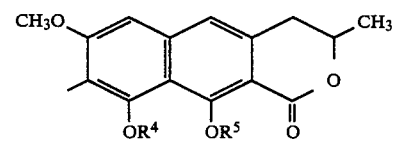

in which R$^4$ and R$^5$ are independently hydrogen or lower alkyl, or a physiologically acceptable salt thereof.

5. The method according to claim 4, wherein R is hydroxy, C$_{1-3}$ alkoxy, amino or amino substituted by C$_{1-3}$ alkyl in the compound.

6. The method according to claim 4, wherein R$^1$ is hydrogen or C$_{1-3}$ alkyl in the compound.

7. The method according to claim 4, wherein R$^2$ is hydroxy, C$_{1-3}$ alkoxy, amino or amino substituted by C$_{1-3}$ alkyl in the compound.

8. The method according to claim 4, wherein each R$^4$ and R$^5$ is hydrogen in the compound.

9. The method according to claim 4, wherein R and R$^2$ are each C$_{1-3}$ alkoxy, amino or amino substituted by C$_{1-3}$ alykl; and R$^1$ and R$^3$ are each hydrogen in the compound.

10. The method according to claim 4, wherein R is amino or amino substituted by C$_{1-3}$ alkyl; and R$^4$ and R$^5$ are each hydrogen in the compound.

11. The method according to claim 4, which further contains a pharmaceutically acceptable carrier or diluent therefor.

* * * * *